US008628585B2

(12) United States Patent
Harris et al.

(10) Patent No.: US 8,628,585 B2
(45) Date of Patent: Jan. 14, 2014

(54) LOWER LIMB PROSTHESIS

(75) Inventors: Graham Harris, Basingstoke (GB);
David Moser, Southhampton (GB); **Mir
Saeed Zahedi**, London (GB)

(73) Assignee: Blatchford Products Limited,
Hampshire (GB)

( * ) Notice: Subject to any disclaimer, the term of this patent is extended or adjusted under 35 U.S.C. 154(b) by 0 days.

(21) Appl. No.: 13/364,786

(22) Filed: Feb. 2, 2012

(65) Prior Publication Data

US 2012/0130508 A1 May 24, 2012

Related U.S. Application Data

(63) Continuation-in-part of application No. 11/956,391, filed on Dec. 14, 2007.

(60) Provisional application No. 61/454,060, filed on Mar. 18, 2011.

(30) Foreign Application Priority Data

Feb. 3, 2011 (GB) .................................. 1101893.4

(51) Int. Cl.
*A61F 2/74* (2006.01)
*A61F 2/64* (2006.01)
*A61F 2/68* (2006.01)
*A61F 2/66* (2006.01)

(52) U.S. Cl.
USPC ................... 623/27; 623/40; 623/44; 623/47; 623/52

(58) Field of Classification Search
USPC .......................................................... 623/27
See application file for complete search history.

(56) References Cited

U.S. PATENT DOCUMENTS

| 37,637 A | 2/1863 | Parmelee |
| 2,657,393 A | 11/1953 | Haller |

(Continued)

FOREIGN PATENT DOCUMENTS

| CN | 101518473 A | 9/2009 |
| DE | 2101303 | 6/1972 |

(Continued)

OTHER PUBLICATIONS

Search Report for Application No. GB1101893.4 dated May 11, 2011.

(Continued)

*Primary Examiner* — David Isabella
*Assistant Examiner* — Jacqueline Woznicki
(74) *Attorney, Agent, or Firm* — Alston & Bird LLP

(57) ABSTRACT

In a lower limb prosthesis an ankle unit has a combination of an hydraulic piston and cylinder assembly providing a continuously damped range of ankle flexion and a resilient telescopic shock absorber. The damping resistance of the piston and cylinder assembly is the predominant resistance to ankle flexion and is provided by a piston which is axially moveable in a cylinder centered on the shin axis. The wall of the cylinder has a cylindrical outer bearing surface for a sleeve which is translationally displaceable relative to the piston and cylinder assembly according to the axial load, the sleeve being resiliently mounted by a compression spring which extends axially within the sleeve and has an integral end portion forming an upper bulkhead of the cylinder. The sleeve is also rotatable on the cylinder wall, the spring providing torsional resistance.

16 Claims, 2 Drawing Sheets

(56) References Cited

U.S. PATENT DOCUMENTS

| | | | |
|---|---|---|---|
| 2,699,554 A | 1/1955 | Comelli | |
| 2,851,694 A | 9/1958 | Capella | |
| 3,871,032 A | 3/1975 | Karas | |
| 4,051,558 A | 10/1977 | Vallotton | |
| 5,030,239 A * | 7/1991 | Copes | 623/52 |
| 5,044,360 A * | 9/1991 | Janke | 602/16 |
| 5,116,383 A * | 5/1992 | Shorter et al. | 623/49 |
| 5,383,939 A | 1/1995 | James | |
| 5,458,656 A | 10/1995 | Phillips | |
| 5,957,981 A | 9/1999 | Gramnas | |
| 6,033,440 A | 3/2000 | Schall et al. | |
| 6,080,197 A | 6/2000 | Chen | |
| 6,187,052 B1 | 2/2001 | Molino et al. | |
| 6,443,993 B1 | 9/2002 | Koniuk | |
| 6,517,585 B1 | 2/2003 | Zahedi et al. | |
| 6,863,695 B2 | 3/2005 | Doddroe et al. | |
| 7,985,265 B2 | 7/2011 | Moser et al. | |
| 2002/0052663 A1 | 5/2002 | Herr et al. | |
| 2002/0082712 A1 | 6/2002 | Townsend et al. | |
| 2002/0120349 A1 | 8/2002 | Phillips | |
| 2002/0138153 A1 | 9/2002 | Koniuk | |
| 2004/0044417 A1 | 3/2004 | Gramnas | |
| 2004/0054423 A1 | 3/2004 | Martin | |
| 2004/0236435 A1 | 11/2004 | Chen | |
| 2005/0109563 A1 | 5/2005 | Vitale et al. | |
| 2005/0192677 A1 | 9/2005 | Ragnarsdottir et al. | |
| 2005/0267601 A1 | 12/2005 | Chen | |
| 2006/0069448 A1 | 3/2006 | Yasui | |
| 2006/0069449 A1 | 3/2006 | Bisbee et al. | |
| 2006/0235544 A1 | 10/2006 | Iversen et al. | |
| 2006/0249315 A1 | 11/2006 | Herr et al. | |
| 2007/0043449 A1 | 2/2007 | Herr et al. | |
| 2008/0262635 A1 | 10/2008 | Moser et al. | |
| 2008/0281435 A1 | 11/2008 | Abimosleh et al. | |
| 2008/0300692 A1 | 12/2008 | Moser et al. | |

FOREIGN PATENT DOCUMENTS

| | | |
|---|---|---|
| EP | 0 549 855 B1 | 3/1996 |
| EP | 0 948 947 | 10/1999 |
| EP | 1 068 844 A1 | 1/2001 |
| GB | 643734 | 9/1950 |
| GB | 2 328 160 A | 2/1999 |
| JP | 59183747 | 10/1984 |
| JP | 59189843 | 10/1984 |
| JP | 2001-514925 A | 9/2001 |
| JP | 2004-506480 A | 3/2004 |
| JP | 2008-536614 T | 9/2008 |
| JP | 2009-515628 A | 4/2009 |
| WO | WO 93/06795 A1 | 4/1993 |
| WO | WO 96/25898 | 8/1996 |
| WO | WO 99/00075 | 1/1999 |
| WO | WO 00/76429 | 12/2000 |
| WO | WO 02/15826 A1 | 2/2002 |
| WO | WO 03/086245 A2 | 10/2003 |
| WO | WO 2006/112774 A1 | 10/2006 |
| WO | WO 2007/027808 A2 | 3/2007 |
| WO | WO 2007/054736 A2 | 5/2007 |
| WO | WO 2008/071975 A1 | 6/2008 |
| WO | WO 2008/103971 A1 | 8/2008 |

OTHER PUBLICATIONS

Combined Search and Examination Report for Great Britain Application No. GB1201875.0 dated Apr. 12, 2012.
Endolite Global—Echelon VT Foot—Prescription [online][retrieved May 7, 2012]. Retrieved from the Internet: <URL: http://www.endolite.co.uk/products/feet/echelon_vt/echelon_vt_foot.html>. 1 page.
International Search Report and Written Opinion for International Application No. PCT/US2008/054741, mailed Jul. 2, 2008.
International Search Report and Written Opinion for International Application No. PCT/GB2012/000112, mailed May 5, 2012.
Office Action for U.S. Appl. No. 13/150,694; dated Dec. 14, 2012.
Hydraulik Ankle Unit Manual; Mauch Laboratories, Inc.
*Anatomic and Biomechanical Characteristics of the Ankle Joint and Total Ankle Arthroplasty*, Total Ankle Arthroplasty, Dec. 5, 2005, Springer Vienna, ISBN 978-3-211-21252 (print) 978-3-211-27254-1 (online), pp. 25-42.
Hayes, W. C. et al.; "*Leg Motion Analysis During Gait by Multiaxial Accelerometry: Theoretical Foundations and Preliminary Validations;*" Journal of Biomechanical Engineering, vol. 105 (1983) pp. 283-289.
Morris, J.W.; "*Accelerometry—A Technique for the Measurement of Human Body Movements;*" Journal of Biomechanics (1973) pp. 726-736.
Office Action for Japanese Application No. 2009-551033 dated Sep. 11, 2012.
Office Action for U.S. Appl. No. 11/956,391; dated Jul. 30, 2013.

* cited by examiner

LOWER LIMB PROSTHESIS

CROSS-REFERENCE TO RELATED APPLICATIONS

This application is a continuation-in-part of currently pending U.S. patent application Ser. No. 11/956,391, filed Dec. 14, 2007. The present application also claims priority from U.S. Provisional Patent Application No. 61/454,060, filed Mar. 18, 2011. The entire contents of the '391 and '060 applications are expressly incorporated herein by reference.

FIELD OF THE INVENTION

This invention relates to a lower limb prosthesis comprising a shin component, a foot component, and an ankle joint mechanism interconnecting the shin and foot components. The ankle joint mechanism is arranged to allow limited damped pivoting movement of the shin component relative to the foot component. The invention also includes a prosthetic ankle unit.

BACKGROUND OF THE INVENTION

Current prosthetic foot and ankle systems are generally aligned for operation as fixed mechanical structures comprising elastic and deformable elements designed to provide stability during standing and walking and to return energy for propulsion into the swing phase of the walking cycle. However, such a device is often uncomfortable for the user whilst standing and whilst walking on ramps and stairs and walking at different speeds. Users have also experienced knee instability and difficulty in maintaining forward motion during roll-over of the foot while standing and walking on ramps and stairs, with consequent impairment of efficiency. These difficulties are particularly important for transfemoral amputees whose stance phase action is normally compromised by significantly reduced knee flexion and extension which would otherwise assist shock absorption and forwards propulsion during the stance phase.

An ankle joint mechanism allowing dynamic hydraulic control of the angular position of a prosthetic foot with respect to a shin component is disclosed in Mauch Laboratories, Inc., Hydraulik Ankle Unit Manual, March 1988. The shin component is attached to a vane piston housed in a fluid-filled chamber with a concave part-circular lower wall. A gravity-controlled ball rolls forwards and backwards on the wall according to the orientation of the foot to open or close a bypass passage in the piston. As a result, dorsi-flexion of the mechanism is prevented when the shin component is vertical, largely irrespective of whether the foot is horizontal or inclined downwardly or upwardly. Such a prosthesis also suffers partly from the disadvantages described above.

Amongst other known prosthetic ankle systems is that of U.S. Pat. No. 3,871,032 (Karan). This system contains a damping device having a dual piston and cylinder assembly with tappet return springs acting continuously to return the ankle to a neutral position. EP-A-0948947 (O'Byrne) discloses a prosthetic ankle having a ball-and-socket joint with a chamber filled with a silicone-based hydraulic substance, the joint having a visco-elastic response. In one embodiment, the chamber contains solid silicone rubber particles suspended in a silicone fluid matrix. US2004/0236435 (Chen) discloses an hydraulic ankle arrangement with adjustable hydraulic damping and resilient biasing members mounted anteriorly and posteriorly of an ankle joint rotation axis. In WO00/76429 (Gramtec), a leg prosthesis is described having an ankle joint allowing heel height adjustment by way of an hydraulic piston and linkage arrangement. Elastic components absorb shock during walking. US2006/0235544 (Iversen et al) discloses an hydraulic ankle mechanism with a rotary vane.

An ankle joint mechanism providing a continuously hydraulically damped range of ankle flexion and in which the damping resistance is the predominant resistance to flexion is disclosed in WO 2008/071975 (Moser et al) and the above-referenced '391 application.

It is also known to incorporate a shock-absorbing unit in a lower limb prosthesis shin component as disclosed, for instance, in GB2234907 (Harris) and GB2305363 (Aulie et al).

SUMMARY OF EMBODIMENTS OF THE INVENTION

According to a first aspect of this invention, a lower limb prosthesis comprises a shin component defining a shin axis, a foot component, and an ankle joint mechanism coupling the shin component to the foot component, wherein the ankle joint mechanism provides a continuously hydraulically damped range of ankle flexion and is constructed and arranged such that, over at least part of the range, the damping resistance is the predominant resistance to flexion, and wherein the shin component has a superior part and an inferior part which are resiliently interconnected so as to be translationally displaceable relative to each other according to the axial compressive load on the shin component, the direction of relative displacement being substantially vertical when the foot component is at rest in an unloaded state on a horizontal supporting surface. The mechanism can comprise an hydraulic linear piston and cylinder assembly. The piston may have distal connection means for pivotal connection to a foot component, the cylinder having proximal connection means for connection to a shin component. Typically, the piston and cylinder assembly has a central axis which is oriented such that when the mechanism is coupled to a prosthetic shin component, the central axis is substantially aligned with or parallel to a shin axis defined by the shin component.

In one embodiment of the invention, the shin component is in the form of a telescopic unit in which the superior shin component part and the inferior shin component part respectively comprise an outer sleeve and a cylindrical housing which is slidably received in the sleeve. The ankle joint mechanism comprises an hydraulic piston and cylinder assembly incorporated in the cylindrical housing so as to lie within the cylindrical envelope defined by the cylindrical housing. This allows the sleeve to overlap at least part of the piston and cylinder assembly when the telescopic unit is fully compressed. The result is a particularly compact unit, especially in terms of the overall extent of the combination of the telescopic unit and the ankle joint mechanism in the superior-inferior direction. Where the ankle joint mechanism comprises a linear piston and cylinder assembly, the cylinder of the assembly in one embodiment has an upper bulkhead and a lower bulkhead, with a cylinder wall joining the upper and lower bulkheads. The cylinder is divided into upper and lower variable volume chamber parts separated by a piston and interconnected by at least one bypass passage incorporating a valve, the or each valve being located in the lower bulkhead for compactness. Each bypass passage is confined within the said cylindrical envelope, each typically comprising a bore in the cylinder wall parallel to the central axis of the piston and cylinder assembly.

A particularly simple and compact arrangement in accordance with one embodiment of the invention includes, as the resilient interconnection in the telescopic unit, an axial compression spring one end portion of which comprises the upper bulkhead of the cylinder of the piston and cylinder assembly. The coil spring and the upper cylinder bulkhead may, accordingly, be constituted by a monolithic element received in the cylindrical housing of the inferior shin component part. Advantageously, the spring not only acts to resist translation relative displacement of the shin component parts, but also acts as a torsion spring resisting rotational relative displacement. In this case, the coil spring has first and second ends secured against rotation respectively in the superior and inferior shin component parts.

In the embodiment having the telescopic unit, the shin component parts are slidable relative to each other in the direction of a telescopic unit centre line, this centre line also being substantially aligned with or parallel to the shin axis. Typically, the ankle joint mechanism defines a medial-lateral ankle joint flexion axis positioned such that the telescopic unit centre line passes within 30 mm of the ankle joint flexion axis, preferably to the posterior of the latter. In terms of the relationship between the telescopic unit and the foot component, the unit is preferably located such that the centre line passes through the foot component at a distance of between 0.2 L and 0.4 L to the anterior of the posterior extremity of the foot component, where L is the overall length of the foot component between its anterior and posterior extremities.

The ankle joint mechanism defines an ankle joint flexion range extending from a dorsi-flexion limit to a plantar-flexion limit. Typically, these flexion limits are, respectively, between 2° and 5° and between 5° and 8° with respect to a mid-stance condition of the ankle joint mechanism. Between these dorsi- and plantar-flexion limits, the ankle joint mechanism is substantially inelastic in the sense that it is not resiliently biased. Consequently, over significant portions of the gait cycle, reaction moments about the ankle are largely dissipated with the result that voluntary control and proprioception by the amputee is improved. The applicants have found that such an ankle joint mechanism allows the amputee, in general, to impose greater axial loads on the prosthesis, the angular yield of the mechanism allowing the foot to align at different shin orientations, with the result that the extra loads on the prosthesis do not add to knee moments to the same degree as with an ankle mechanism which is rigid over much of the gait cycle. As a consequence, the resilient shock-absorbing shin component provides enhanced energy storage in the shin, resulting in a more natural gait and greater comfort for the amputee. In addition, such factors encourage the amputee to place a greater load on the prosthetic limb, relieving the strain on the other, natural leg.

To allow individual setting of dorsi and plantar-flexion damping resistances, the ankle joint mechanism may have a valve arrangement controlling the flow of hydraulic fluid between chambers of the piston and cylinder on opposite sides of the piston, the valve arrangement for example comprising first and second adjustable valves for dorsi-flexion and plantar flexion damping control respectively. Accordingly, the ankle joint mechanism provides a variable-resistance continuously hydraulically damped range of ankle flexion, the mechanism being constructed and arranged such that, over at least part of the range, movement in the dorsi and plantar directions being substantially unbiased resiliently over at least part of the range.

The ankle joint mechanism can include a mechanical end stop limiting dorsi flexion of the ankle joint mechanism, resulting in the shin component having an anterior tilt of at least 3° with respect to the vertical when the joint mechanism is flexed to the dorsi-flexion limit. The mechanical end stop is operative by the abutment of one part of the prosthesis associated with the shin component against another part of the prosthesis associated with the foot component. Conveniently, the end stop is defined by the piston of the piston and cylinder assembly abutting an end wall of the cylinder.

In the exemplary embodiment of the invention described hereinafter, the range of damped ankle flexion is fixed. Nevertheless, the above-mentioned dorsi-flexion limit may be adjustable over at least a range of anterior-posterior tilt angles from 3° to 5°. In another embodiment, the range of damped flexion may alter when the dorsi-flexion limit is adjusted, but once the adjustment has been made, the range of damped flexion is, likewise, fixed from step to step.

The prosthesis may be arranged such that the relative position of the foot component and the shin connection interface at the dorsi-flexion limit is defined independently of the orientation of the assembly in space.

Adjustment of the shin axis orientation in the anterior-posterior direction with respect to the foot component may be performed using at least one conventional pyramid alignment interface, preferably on the superior shin component part.

The combination of the ankle joint mechanism referred to above and the resiliently compressible shin component operates especially well with an energy-storing foot component having, for instance, a fibre-reinforced plastics leaf spring that is resiliently deformable to allow dorsi-flexion of at least an anterior portion of the foot component relative to an ankle-mounting portion of the foot. The foot spring is arranged to be deflected when dorsi-flexion load is applied to the foot anterior portion and the ankle joint mechanism has reached its dorsi-flexion limit. The ankle joint mechanism and the foot component together constitute a Maxwell-model damper/spring combination of which the damper element is the said ankle joint mechanism and the spring element is a spring component arranged in series with the ankle joint.

As stated above, the shin component can comprise a telescopic unit that not only provides resilient compression of the shin component under load, but also allows rotation of the inferior part of the shin component relative to the superior part about e.g. a substantially vertical axis, i.e. the centre line of the unit and the shin axis. Both axial and torsional resilience can be provided by a single coil spring. However, it is also possible for the coil spring to provide axial resilience alone, the spring having one end seated in the inferior part and the other end seated in the superior part, one or both spring ends being free to rotate relative to the part in which it is seated. Torsional resilience may be provided separately by using an elastic bar made of, for instance, a resilient thermoplastics material such as a nylon-based plastics material (e.g. Delrin) located on the telescopic unit centre line, each end of the bar being secured against rotation in the respective shin component part, but free to move longitudinally and axially in at least one of such parts.

Described below is a lower limb prosthesis comprising a resiliently compressible shin component defining a shin axis, a foot component, and an ankle joint mechanism interconnecting the shin and foot components and arranged to allow limited damped pivoting of the shin component relative to the foot component about a medial-lateral joint flexion axis during use, wherein the ankle joint mechanism comprises: a piston and cylinder assembly the piston of which is movable so as define a variable-volume fluid-filled chamber of the assembly, fluid being admitted to or expelled from the chamber through at least one damping orifice as the relative orientation of the shin and foot components varies with flexion of the joint mechanism; and flexion limiting means limiting dorsi-flexion of the joint mechanism to a dorsi-flexion limit corresponding to orientation of the shin component with the shin axis tilted anteriorly with respect to the vertical by at least 3 degrees. The ankle joint mechanism can be arranged such that damped relative pivoting of the shin component and the foot component is allowed over an angular range between dorsi- and plantar-flexion limits, the dorsi-flexion limit being adjustable to different anterior tilt settings of the shin axis with respect to the foot component. In particular, the angular range encompasses a foot-flat, shin-axis-vertical state with the permitted degree of shin axis tilt being adjustable to different values to the anterior of the vertical.

In one particular embodiment of the invention, the joint mechanism has a first part associated with the shin component and a second part associated with the foot component, these two parts being pivotally interconnected, such interconnection defining a joint flexion axis. One of the two parts includes the chamber of the piston and cylinder assembly and the other is pivotally connected to the piston, the mechanism being arranged such that the dorsi-flexion limit is defined by a mechanical stop limiting relative rotation of the first and second parts. This mechanical stop may be the abutment of the piston with an end surface of the chamber. A cushioning spring or pad may be applied to the top surface of the piston or to the opposing chamber surface in order to increase the resistance to dorsi-flexion as the dorsi-flexion limit is approached.

The dorsi-flexion limit is typically fixed, i.e. non-adjustable. However, as an alternative, the limit may be preset. For instance, the limit may be set by an adjustable anterior-posterior tilt alignment interface. The interface may be of the well-known inverted pyramid construction as described above. Another possibility is a lockable pivot joint for connecting the foot component to the joint mechanism, having an adjustment axis running in the medial-lateral direction. As a further alternative, an adjustable end stop may be provided in the piston and cylinder assembly, or the connection between the piston and one of the components of the mechanism mounting the foot component or the shin component may be adjustable to alter the range of displacement of the piston in the chamber of the assembly with respect to the angular range of movement of the foot component relative to the shin component.

The joint mechanism in one embodiment includes two passages in communication with the above-mentioned chamber of the piston and cylinder assembly, each containing a respective non-return valve, one oriented to prevent the flow of fluid from the chamber through its respective passage and the other oriented to prevent the admission of fluid to the chamber through the other passage, so that one permits fluid flow when the joint mechanism is flexing in the direction of dorsi-flexion while the other passage permits the flow of fluid when the joint is flexing in the direction of plantar-flexion. As an example, both passages can have respective adjustable-area damping orifices to allow the degree of damping to be tuned to the user's requirements.

A locking device may also be provided for locking the joint mechanism against pivoting at any of a number of positions of the foot component relative to the shin component. Typically this is performed using a manually or electromechanically operated valve which interrupts the flow of fluid to or from the above-mentioned chamber of the piston and cylinder assembly through the bypass passages. The locking device comprises a control member having two positions, one in which the joint mechanism operates in a yielding mode and one in which it operates in a locked mode. Retaining means are provided for retaining the control member in either of the two positions, e.g. a spring biasing the control member into one position and a detent, latch or lock for keeping the control member in the other position.

According to a second aspect of the invention, there is provided a prosthetic ankle unit comprising the combination of an hydraulic linear piston and cylinder assembly providing a continuously damped range of ankle flexion and defining a central axis, the assembly including a cylinder wall centred on the axis and enclosing a fluid-filled chamber the volume of which varies with movement of a piston therein, and a telescopic shock absorber which is coaxial with the piston and cylinder assembly and comprises an outer sleeve which is slidably received on the outside of the cylinder wall and resiliently connected thereto so as to be translationally displaceable relative to the cylinder wall according to the axial load applied to the sleeve, the sleeve overlapping at least part of the fluid-filled chamber when the shock absorber is fully compressed.

The invention will be described below by way of example with reference to certain exemplary embodiments of the invention as depicted in the drawings.

DETAILED DESCRIPTION OF THE DRAWINGS

Figure 1:
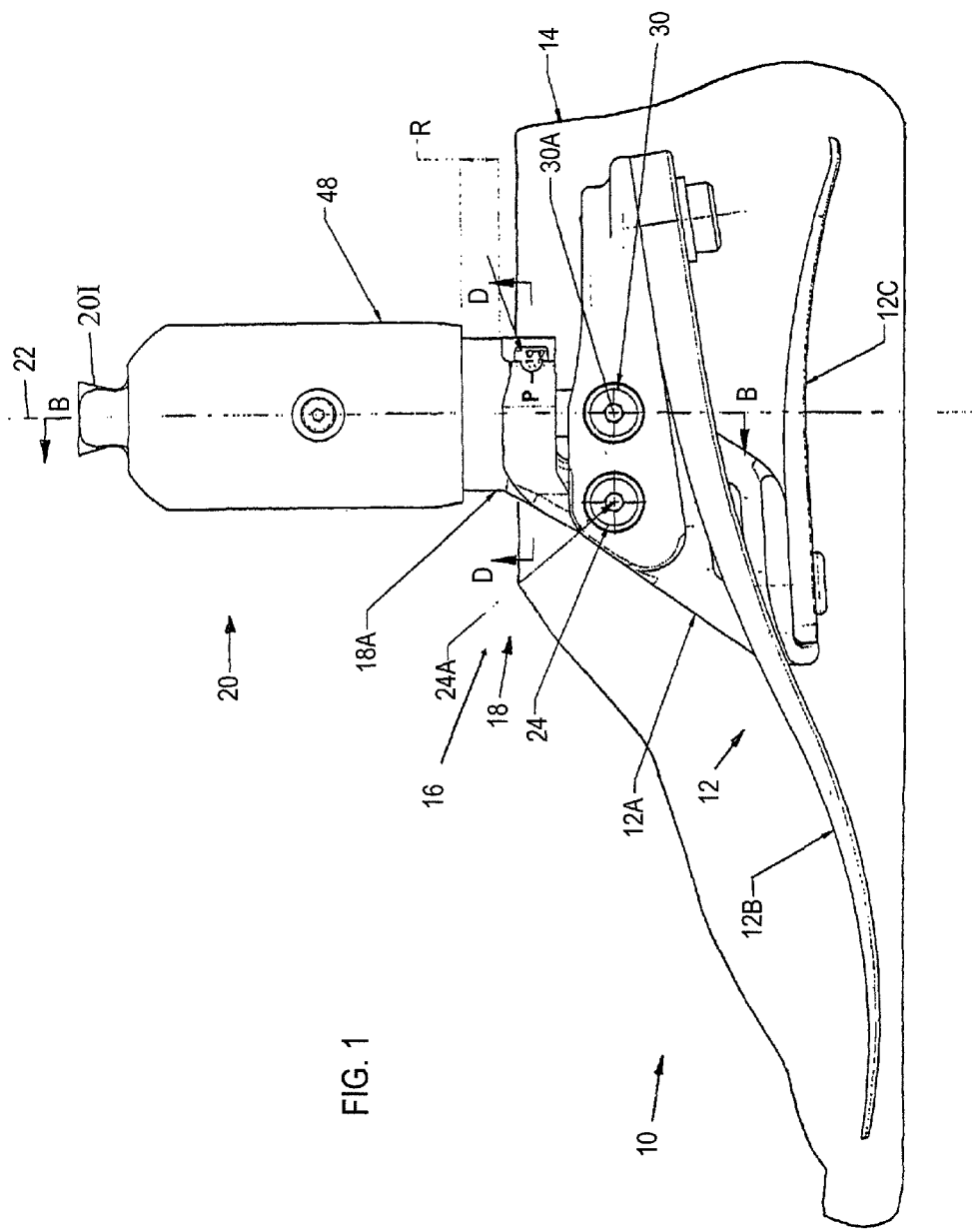
FIG. 1 is a lateral side view of a prosthetic assembly for a lower limb prosthesis in accordance with one embodiment of the invention, including superior and inferior shin component parts, an ankle unit, and an energy-storing foot component.
Figure 2:
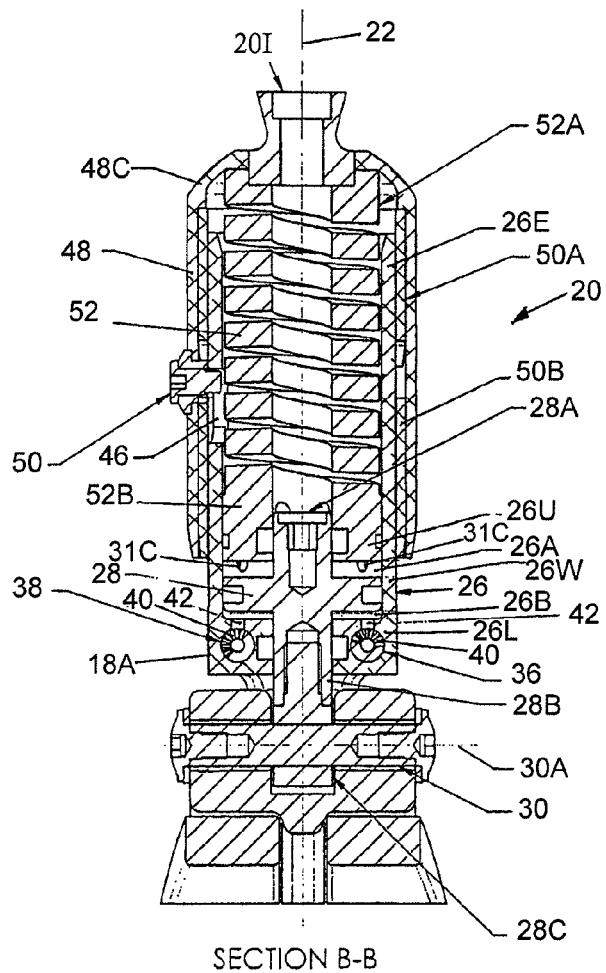
FIG. 2 is a cross-sectional posterior view of the shin component parts and the ankle joint mechanism, taken on a plane containing the axis of the shin component parts.
Figure 3:
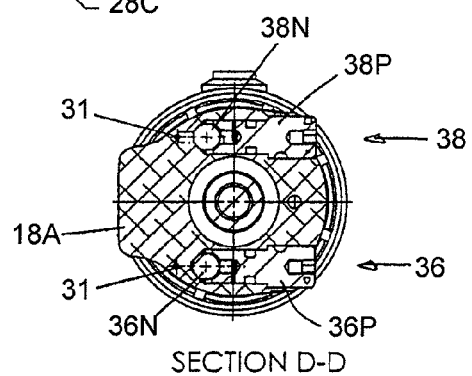
FIG. 3 is a transverse cross-section of the assembly showing FIGS. 1 and 2, viewed from below and taken on a plane through the inferior shin component part.

Referring to FIGS. 1 to 3, a lower limb prosthesis in accordance with one embodiment of the invention has a foot component 10 with a foot keel 12 comprising a rigid carrier 12A, and a toe spring 12B and a heel spring 12C as fibre-reinforced plastics leaf springs independently coupled to the carrier 12A. The keel 12 is surrounded by a foam cosmetic covering 14.

Mounted to the foot keel 12 is an ankle unit comprising an ankle joint mechanism 18 which mounts a shin component 20. The shin component 20 defines a longitudinal shin component axis 22. The shin component 20 typically forms part of a longer prosthetic shin, the remainder of the shin, which is not shown in the drawing, being connected to the shin component 20 by a conventional pyramidal alignment interface 20I. The mounting of the ankle unit 18 to the foot keel 12 is by way of an ankle flexion pivot shaft 24 defining an ankle joint flexion axis 24A running in a medial-lateral direction to the anterior of the shin component axis 22.

The body 18A of the ankle unit forms the cylinder wall 26W and lower bulkhead 26L of the cylinder 26 (FIG. 2) of a piston and cylinder assembly. This assembly has a piston 28 with upper and lower piston rods 28A, 28B, the lower piston rod being pivotally connected to the foot keel 12 at a second pivotal connection in the form of a pivot shaft 30 secured in a trunnion 28C on the lower piston rod 28B, this second pivotal connection defining a second medial-lateral axis 30A which is spaced, in this case, posteriorly from the flexion axis 24A. It will be seen that as the body 18A of the ankle unit pivots about the flexion axis 24A, the piston 28 moves substantially linearly in the cylinder 26.

The cylinder 26 of the piston and cylinder assembly has an upper bulkhead 26U fixed in the cylindrical housing formed by the ankle unit body 18A. The piston 28 divides the cylinder interior into upper and lower chambers 26A, 26B. These chambers are linked by two bypass passages 31 (FIG. 3) the major parts of which extend longitudinally in the cylinder wall 26W. Cross-drillings 31C in the cylinder wall 26W complete the connections to the upper cylinder chamber 26A. These two bypass passages 31, 31C communicate with the lower chamber 26B of the cylinder via respective damping resistance control valves 36, 38 each having a manually adjustable orifice area and each containing a non-return valve 36N, 38N. Each control valve 36, 38 has a manually rotatable plug 36P, 38P, each plug having a blind internal axial bore and a plurality of radial passages 36R, 38R of differing cross-sectional areas. In each case, when the plug 36P, 38P is rotated in the bulkhead 26L, different radial passages 40 come into registry with a respective port 42 opening out into the lower chamber 26B of the cylinder 26. The non-return valves 36N, 38N are biased in opposite directions so that one of the control valves 36 controls the damping of the piston and cylinder assembly in the direction of dorsi-flexion and the other control valve 38 controls damping of the assembly in the direction of plantar-flexion. More particularly, the control valve 36 has its non-return valve 36N oriented to allow the flow of hydraulic fluid from the lower chamber 26B to the upper chamber 26A. The other control valve 38 has its non-return valve 38N oriented in the opposition direction so as to allow the flow of hydraulic fluid from the upper chamber 26A to the lower chamber 26B. Accordingly, the orifice area of one of the control valves, valve 36, is operative during dorsi-flexion, and orifice area of the other, valve 38, during plantar-flexion. (In each valve 36, 38, the adjustable area orifice and the non-return valve are arranged in series in the bypass passage interconnecting the upper and lower chamber parts 26A, 26B.)

The piston and cylinder assembly allows damped continuous yielding movement of the foot component 10 relative to the ankle unit 16 about the flexion axis 24A between dorsi-flexion and plantar-flexion limits defined by the abutment of the piston with, respectively, the lower bulkhead and the upper bulkhead of the cylinder 26. The level of damping for dorsi-flexion and plantar-flexion is independently and manually presetable by the respective adjustable-area orifices, as described above.

Integrated with the ankle joint mechanism 18, the shin component 20 comprises a telescopic unit permitting resilient axial and rotational movement. The telescopic unit is generally cylindrical, its central axis defining the shin component axis 22 which also coincides with the central axis of the cylinder 26. Details of the telescopic unit will be described herein below. With regard to ankle joint flexion, the limit of dorsi-flexion of the ankle joint mechanism, defined by the abutment of the piston 28 with the lower bulkhead 26L of the cylinder 26, corresponds to an anterior tilt of the shin component axis 22 relative to the vertical when the user stands on a horizontal surface. The plantar-flexion limit, defined by abutment of the piston 28 with the upper bulkhead 26U of the cylinder 26 corresponds to a posterior tilt of the shin component axis 22.

In this embodiment, the anterior and posterior tilt angles of the shin component axis 22 at the dorsi-flexion and plantar-flexion limits are 4 degrees (anterior) and 7 degrees (posterior) respectively with respect to the vertical. The mechanical end-stops represented by the abutment of the piston 28 with the lower and upper cylinder bulkheads define a yield range over which the ankle-foot prosthesis is free to flex during locomotion and during standing.

In this embodiment, the shin component 20 includes an adjustable shin connection interface 201 having an inverted pyramid shaped to be received in an annular female pyramid receptacle having alignment screws, as well known to those skilled in the art, for adjusting the orientation of the interconnected components. In such an embodiment, at a neutral alignment position, the axis of the remaining portion of the prosthetic shin (not shown) is coincident with the axis 22 of the shin component 20. Alteration of the shin tube alignment at such a connection interface does not alter the angular magnitude of the ankle yield range because it is governed by the piston stroke, but it does alter the position of the ankle joint flexion limits with respect to the vertical.

It will be understood, therefore, that the angular range magnitude is fixed by the construction and geometry of the prosthesis and its hydraulic joint mechanism.

The ankle joint mechanism 18 and its connection to the foot component 10 are similar to the foot and ankle prosthesis described in the above-referenced '391 application. This earlier-dated application sets out further details of an ankle joint mechanism that functions in the same way as the ankle joint mechanism disclosed in the present application. The present prosthesis shares a number of advantages with the prosthetic assembly disclosed in the earlier application. For example, since the ankle joint mechanism allows dorsi-plantar flexion over a limited range of movement with largely damped, as opposed to resilient, resistance to motion, the ankle is able easily to flex under load according to changing activity requirements without generation of high reaction moments which would otherwise cause discomfort and compromise the function of the prosthesis. Providing damped and substantially unbiased movement means that the ankle thereby functions in a way such that it remains in its last loaded orientation, having no re-alignment capability once the foot is unloaded. This feature is advantageous to assist foot clearance during the swing phase.

By arranging for the position of the foot component relative to the shin component at the dorsi-flexion limit to be defined independently of the orientation of the assembly in space, and by using gravity-independent determination of the dorsi-flexion limit, the need for a gravity-dependent valve system with an end-stop corresponding to vertical orientation of the shin axis is avoided. This prosthesis allows set-up flexibility to alter the dynamics of roll-over through selection of different toe spring stiffnesses. The range of yielding motion can be altered by altering the relative alignment of the foot and shin components. Allowing the shin axis to move to the anterior of the vertical position is particularly advantageous during stair and ramp walking activities.

The conventional approach of maximising energy storage and return has produced designs in which the ankle has a high elastic stiffness at all times. Reducing stiffness in the manner proposed improves comfort for the user as well as helping to preserve forwards momentum of the upper body and thus locomotion efficiency. Reaction moments about the ankle are largely dissipated with the result that voluntary control and proprioception of the knee and hip in BK (below-knee) amputees, in particular, is improved.

The shin component 20, embodied as a telescopic unit, is now described with reference to FIG. 2.

The shin component 20 is in two parts: an upper or superior part incorporating the alignment interface pyramid 201, and a lower part formed by the body 18A of the ankle joint mechanism 18.

The lower shin component part, formed by the body 18A of the ankle joint mechanism 18, has a hollow upper cylindrical extension 26E of the cylinder wall 26W of the piston and cylinder assembly 26, 28. Indeed, the outside diameter of the upper extension 26E is the same as the outside diameter of the cylinder wall 26W and the ankle body 18A in the region of the piston and cylinder assembly. The cylindrical extension 26E has an aperture 46 on one side in the form of a slot. Surrounding the cylindrical extension 26E is a cylindrical outer sleeve 48 and integral upper cap 48C incorporating the alignment interface pyramid 20I. Secured to the inner surface of the outer sleeve 48 is a cylindrical bearing lining which is in two parts 50A, 50B and which slides on the inner cylindrical extension 26E. Housed in the outer sleeve 48 is an inwardly projecting spigot 50 which is in registry with the aperture 46 in the cylindrical extension 26E, abutment of the spigot 50 with the edges of the aperture serving to limit the freedom of movement of the outer sleeve 48 on the inner cylindrical extension 26E. The outer sleeve 48 is free not only to move axially (i.e. executing translational displacement parallel to the axis 22), but also to rotate about the shin component axis 22.

Housed within the cylindrical extension 26E is an axially oriented coil spring 52 having an upper end portion 52A secured against rotation in the outer sleeve cap 48C. The spring also has a tubular lower end portion 52B of sufficient bulk to form a rigid ring secured rigidly in the cylindrical extension 26E and cylinder wall 26W so as to form the upper bulkhead 26U of the piston and cylinder assembly cylinder 26. In this embodiment of the invention, the upper cylinder bulkhead 26U and the remainder of the spring 52, including the upper end portion 52A, are integrally formed from a single metal billet. The spring 52, accordingly, forms a compact resilient and structural element biasing the outer sleeve 48 against both translational and rotational displacement from an unloaded position relative to the cylindrical extension 26E. The lower end portion 52B of the spring 52, forming the upper cylinder bulkhead 26U, has a central bore of a diameter such as to receive the upper piston rod 28A so that the latter can slide axially and execute a slight rocking movement, as required by the geometry of the ankle joint mechanism.

In this embodiment, the range R (FIG. 1) of relative translational displacement allowed by the telescopic unit is about 5mm. In general, a relative translational displacement range of between 4mm to 8mm is typical. When unloaded, the outer sleeve 48 and the ankle unit body 18A are biased apart by the spring 52 so that the spigot 50 is adjacent an upper edge of the aperture 46.

The spring 52 resiliently resists rotation of the outer sleeve 48 relative to the ankle unit body 18A in either direction from a neutral, unloaded position.

As will be seen from the drawing, the centre line of the telescopic unit defined by the shin component is substantially vertical when the foot 10 is at rest on a horizontal surface when the ankle joint mechanism is at a neutral position, i.e. at an intermediate position between dorsi-flexion and plantar flexion, this being the condition of the ankle joint mechanism at mid-stance and when the amputee is standing normally on a horizontal surface. In this condition, the ground vector and load line pass to the posterior of the ankle joint flexion axis 24A and approximately parallel to the telescopic unit centre line, represented here by the shin component axis 22.

In this embodiment, the telescopic unit centre line lies about 22 mm behind the ankle joint flexion axis (and the load line at rest passes about 10 mm behind the axis).

Owing to the manner in which the ankle joint mechanism is self-aligning insofar as it accommodates dorsi- and plantar-flexion within the above-described limits without resilient biasing, the amputee is able to place significantly greater vertical loads on the prosthesis and, indeed, as the ankle joint mechanism flexes in the dorsi and plantar directions, this increase in loading can be achieved over significant portions of the gait cycle, whether the shin component axis 22 (and the telescopic unit centre line) is vertical or not, with the result that increased energy is stored in the spring 52, to be released at push-off. Self-alignment of the ankle joint mechanism 18 results in the telescopic unit centre line being more nearly parallel to the ground reaction vector over much of the gait cycle than is achieved with a rigid ankle or an ankle that is predominantly elastic rather than damped.

As will be seen from the drawings, the telescopic unit centre line, in this case the shin component axis 22, passes through the foot component at a distance to the anterior of the posterior extremity of the foot component (i.e. the rear of the heel) by a distance equal to about one third of the total length of the foot component.

The dynamic action of the prosthesis during walking will now be briefly described. At heel strike, the ankle is in a dorsi-flexed state from the roll-over actions of the previous step. As the load on the prosthesis increases, the ground reaction force on the heel spring 12C causes the telescopic unit to compress at the same time as the heel spring is deflected, storing compression energy in both the latter and the axial spring 54. Concurrently, the ankle joint rotates towards plantar-flexion as a result of a lever action of the ground reaction force exerted on the heel spring, and the foot moves towards a foot-flat state. The combination of hydraulic damping resistance against such rotation and the resistance of the heel spring 12C and the axial spring 54 produces a smooth and progressive transfer of load onto the prosthesis at the commencement of the stance phase. In general, plantar-flexion at the ankle does not reach the plantar-flexion limit imposed by the joint mechanism of the prosthesis at this stage. During rollover and towards toe-off, the main leaf spring 12B starts to deflect. This happens as soon as load is applied to the leaf spring 12B and the resulting movement at the ankle causes hydraulically damped ankle dorsi-flexion, providing a smooth roll-over action, preserving body momentum, and improving knee function. Towards the end of the roll-over phase, the dorsi-flexion limit imposed by the ankle joint mechanism is reached. As this happens, mechanical energy is increasingly directed into the main leaf spring 12B of the foot component to provide energy return for push-off and the telescopic unit of the shin component 20 expands as the energy stored in the axial spring 52 is released, contributing to the push-off. The swing phase is initiated with the foot oriented at the dorsi-flexion end stop to provide toe clearance during the swing phase. At the commencement of the swing phase, the telescopic unit of the shin component 20 is fully expanded. As the yielding components of the prosthesis, i.e. the springs and the ankle joint mechanism, reach their respective limits of travel during the above-described operation of the prosthesis, the relative proportions of their deflections in the overall movement of the shin component upper part vary.

In summary, the lower limb prosthesis described above is a prosthetic system that is continuously allowed to yield over a limited range in plantar- and dorsi-flexion. The yielding action is provided by an hydraulic damper coupled to conventional foot elements (i.e. keel, carrier and independent carbon fibre composite heel-toe springs). The ankle is, therefore, free to flex continuously over a limited plantar- and dorsi-flexion range via the hydraulic damper with minimal interference from elastic elements during walking and standing. During standing, the relative positions of the hip, knee and ankle joint centres are such that substantially normal standing postures can be maintained, the moments about each joint being automatically balanced thereby creating limb stability. Moreover, the self-aligning action of the foot-ankle system facilitates improved control of energy transfer between limb segments during locomotion, the user's hip joint being the main driver and the knee joint being the main facilitator of mechanical energy transfer, energy transfer to and from the telescopic unit of the shin component being further facilitated. This biomimetic method of stabilisation of standing stability and balance control has a further advantage in that, while standing on ramps, owing to the yielding action of the hydraulic components, there are no significant reaction moments generated around the ankle which may cause imbalance between joints and discomfort. Since, owing to the limited range of hydraulic yielding, the ankle is free to move, adaptation for walking and standing on inclined surfaces and changes to footwear with various heel heights is achieved automatically. A further advantage of the system is a smoother more progressive transition during roll-over over a variety of terrains.

With a view to achieving wide applicability of the above-described prosthetic assembly, compactness and, particularly, minimisation of the overall height are achieved by incorporating the hydraulic bypass passages of the piston and cylinder assembly within the diameter of the cylindrical inner part of the telescopic unit so that the outer diameter of the inner part is maintained at least down to the level of the lower bulkhead of the cylinder, thereby allowing the outer sleeve to overlap the cylinder when the telescopic unit is fully compressed. Minimisation of height and simplicity are aided by the integral construction of the coil spring and the upper cylinder bulkhead of the piston and cylinder assembly. Location of the control valves 36, 38 in the lower bulkhead of the piston and cylinder assembly also provides a compact solution. Another beneficial feature is the integral, one-piece construction of the ankle unit body 18A and the cylindrical housing formed by the upper extension 26E of the cylinder wall 26W. Thus, the cylinder wall 26W forms part of the inferior shin component part, having an outwardly facing cylindrical bearing surface which extends downwardly and is in registry with the cylinder chamber of the piston and cylinder assembly. Further space is saved by the elimination of a separate torsion bar spring providing rotational resilience, as well as its associated housings, by using the coil spring as the resilient biasing means for both translation and rotational displacement.

What is claimed is:

1. A lower limb prosthesis comprising a shin component defining a shin component axis, a foot component, and an ankle joint mechanism coupling the shin component to the foot component, wherein the ankle joint mechanism comprises a hydraulic piston and cylinder assembly, the hydraulic piston and cylinder assembly comprising a cylinder having a cylinder wall within which a piston is slidably mounted to move linearly, the hydraulic piston and cylinder assembly providing a continuously hydraulically damped range of ankle flexion and being constructed and arranged such that, over at least part of the range, the damping resistance is the predominant resistance to flexion, and wherein the shin component is in the form of a telescopic unit in which a superior shin component part and an inferior shin component part are resiliently interconnected so as to be translationally displaceable relative to each other according to the axial load on the shin component, the direction of relative displacement being substantially vertical when the foot component is at rest in an unloaded state on a horizontal supporting surface, the superior part and the inferior part respectively comprising an outer sleeve and a cylindrical housing slidably received in the sleeve, the cylindrical housing forming the cylinder wall.

2. A prosthesis according to claim 1, wherein the hydraulic piston and cylinder assembly is incorporated in the cylindrical housing so as to lie within a cylindrical envelope defined by the cylindrical housing, thereby to allow the sleeve to overlap at least part of the piston and cylinder assembly when the telescopic unit is fully compressed.

3. A prosthesis according to claim 2, wherein the hydraulic piston and cylinder assembly has a central axis substantially aligned with the shin component axis.

4. A prosthesis according to claim 3, wherein the cylinder of the piston and cylinder assembly has an upper bulkhead and a lower bulkhead, the cylinder wall joining the upper and lower bulkheads.

5. A prosthesis according to claim 4, wherein the cylinder has upper and lower variable-volume chamber parts separated by the piston and interconnected by at least one bypass passage incorporating a valve, wherein the or each valve is located in the lower bulkhead.

6. A prosthesis according to claim 4, wherein the telescopic unit includes an axial coil spring arranged to be compressed when the unit is subject to an axial load, the coil spring and the piston and cylinder assembly being arranged in a superior-inferior relationship.

7. A prosthesis according to claim 6, wherein the coil spring and the upper bulkhead of the cylinder are constituted by a monolithic element received in the said cylindrical housing.

8. A prosthesis according to claim 6, wherein the coil spring has first and second ends secured against rotation in the superior and inferior shin component parts respectively, and is configured to act both as a compression spring resisting translational relative displacement of the shin component parts and as a torsion spring resisting relative rotation of the shin component parts.

9. A prosthesis according to claim 2, wherein the cylinder has first and second variable-volume chamber parts separated by the piston, and interconnected by at least one bypass passage, the or each bypass passage being confined within said cylindrical envelope.

10. A prosthesis according to claim 1, wherein the ankle joint mechanism defines a medial-lateral ankle joint flexion axis and the shin component parts are slidable relative to each other in the direction of a telescopic unit center line, which center line passes within 30 mm of the ankle joint flexion axis.

11. A prosthesis according to claim 10, wherein the telescopic unit center line is to the posterior of the ankle joint flexion axis.

12. A prosthesis according to claim 10, wherein the telescopic unit center line passes through the foot component at a distance of between 0.2 L and 0.4 L to the anterior of the posterior extremity of the foot component, where L is the overall length of the foot component between its anterior and posterior extremities.

13. A prosthesis according to claim 1, wherein the ankle joint mechanism defines an ankle joint flexion range extending from a dorsi-flexion limit of between 2° and 5° with respect to a mid-stance condition and a plantar-flexion limit of between 5° and 8° with respect to the mid-stance condition.

14. A prosthesis according to claim 1, wherein the cylindrical housing of the shin component is pivotally connected to the foot component for pivoting about an ankle joint flexion axis.

15. A prosthesis according to claim 14, wherein the piston has a piston rod pivotally coupled to the foot component to define a piston rod pivot axis spaced from the ankle joint flexion axis.

16. A prosthesis according to claim 1, wherein the foot component comprises an energy-storing fiber reinforced plastics leaf spring extending from the ankle joint mechanism to a toe section of the foot component.

* * * * *